US 8,535,853 B2

Sep. 17, 2013

(12) United States Patent
Naydenova et al.

(10) Patent No.: US 8,535,853 B2
(45) Date of Patent: Sep. 17, 2013

(54) HOLOGRAPHIC SENSOR

(75) Inventors: Izabela Naydenova, Dublin (IE);
Hosam Sherif, County Kildare (IE);
Suzanne Martin, Dublin (IE);
Raghavendra Jallapuram, Dublin (IE);
Vincent Toal, County Dublin (IE)

(73) Assignee: Dublin Institute of Technology, Dublin (IE)

( * ) Notice: Subject to any disclaimer, the term of this patent is extended or adjusted under 35 U.S.C. 154(b) by 0 days.

(21) Appl. No.: 13/557,529

(22) Filed: Jul. 25, 2012

(65) Prior Publication Data

US 2012/0288785 A1   Nov. 15, 2012

Related U.S. Application Data

(63) Continuation of application No. 12/085,455, filed as application No. PCT/IE2006/000134 on Nov. 27, 2006, now Pat. No. 8,263,291.

(30) Foreign Application Priority Data

Nov. 25, 2005   (IE) .................................. 2005/0784

(51) Int. Cl.
   *G03F 7/04*   (2006.01)
(52) U.S. Cl.
   USPC ............................................................ 430/2
(58) Field of Classification Search
   USPC ................................................... 430/1, 2
   See application file for complete search history.

(56) References Cited

U.S. PATENT DOCUMENTS

| | | |
|---|---|---|
| 2002/0040964 A1 | 4/2002 | Dausmann |
| 2008/0068684 A1 | 3/2008 | Kabilan |

FOREIGN PATENT DOCUMENTS

| | | |
|---|---|---|
| CN | 1329285 A | 1/2002 |
| WO | WO 95/26499 | 10/1995 |

OTHER PUBLICATIONS

I. Naydenova et al., "Investigation of the diffusion processes in a self-processing acrylamide-based photopolymer system," Applied Optics, May 10, 2004, vol. 43, No. 14, pp. 2900-2905.
R. Jallapuram, "Spatial Frequency Response of Acrylamide Based Holographic Photopolymer," Proc. of Intl. Conf. on Laser Applications and Optical Metrology, pp. 275-279.
S. Martin et al., "Applications of a Self-Developing Photopolymer Material: Holographic Interferometry and High Efficiency Diffractive Optical Elements," Optical Memory and Neural Networks, 1998, vol. 7, No. 2, pp. 79-87.
S. Martin et al., "Two way diffusion model for the recording mechanism in a self developing dry acrylamide photopolymer," Holography 2005: Intl. Conf. on Holography, Optical Reading, and Proceeding of Information, Proc. of SPIE vol. 6252, pp. 625205-1-625205-8.
Blaya et al. "Optimal Composition of an Acrylamide and N,N'-Methylenebisacrylamide Holographic Recording Material." Journal of Modern Optics, vol. 45, No. 12, Dec. 1998, pp. 2573-2584.
Calixto. "Dry Polmer for Holographic Recording." Applied Optics, vol. 26, No. 18, Sep. 15, 1987, pp. 3904-3910.

(Continued)

*Primary Examiner* — Lisa Caputo
*Assistant Examiner* — Punam Roy
(74) *Attorney, Agent, or Firm* — Jacobson Holman PLLC

(57) ABSTRACT

A sensor device comprising a holographic element comprises a grating or hologram recorded in a holographic recording medium wherein at least one physical and/or chemical and/or optical characteristic of the holographic element or the image produced by it varies as a result of variation in relative humidity or moisture content in the air surrounding the element. Also provided is an acrylamide-based photopolymer and an acrylamide-based reflection hologram.

17 Claims, 9 Drawing Sheets

(56) References Cited

OTHER PUBLICATIONS

Gong et al. "A Humidity-Resistant Highly Sensitive Holographic Photopolymerizable Dry Film." Materials Letters, vol. 59, No. 23, Oct. 23, 2005, pp. 2969-2972.

Lawrence et al. "Photopolymer Holographic Recording Material." Optik International Journal for Light and Electron Optics. vol. 112, No. 10, 2001, pp. 449-463.

Martin et al. "Holographic Recording Characteristics of an Acrylamide-Based Photopolymer." Applied Optics, vol. 36, No. 23, Aug. 10, 1997, pp. 5757-5768.

Spooncer et al. "A Humidity Sensor Using a Wavelength-Dependent Holographic Filter with Fibre Optic Links." International Journal of Optoelectronics, vol. 7, No. 3, 1992, pp. 449-452.

Weiss et al. "Photopolymeric Holographic Recording Media: In-situ and Real-time Characeterization." Proceedings of the SPIE—The International Society for Optical Engineering Spie-Int., vol. 2699, Online publication Oct. 12, 2004.

International Search Report dated Jul. 23, 2007.

V. Weiss, E. Millul, and A.A. Friesem, "Photopolymeric holographic recording media: in-situ and real-time characterization," Proceedings of the SPIE—The International Society for Optical Engineering SPIE-Int., vol. 2699, Published online on Oct. 12, 2004, pp. 11-21.

RH 60%   RH 40%   RH 20%

HOLOGRAPHIC SENSOR

This application is a Continuation Application of U.S. patent application Ser. No. 12/085,455, filed May 23, 2008, which is a national stage of PCT/IE2006/000134 filed Nov. 27, 2006, which claims priority to Irish patent application 2005/0784 filed Nov. 25, 2005, which is incorporated by reference herein.

The invention relates to a sensor device comprising a holographic element, for sensing and indicating a change in an environmental property, such as relative humidity or moisture content.

In one current approach, relative humidity may be measured by means of a humidity meter device, however, such devices need a power source, or to be connected to a power source and are relatively complex, expensive, and bulky devices which include electronic components. In another approach a card containing spots of silica gel may be provided to indicate a change in relative humidity by a colour change. However, such devices often have a slow response time and limited accuracy and are not suitable for use with foodstuffs.

WO95/26499 describes a holographic sensor based on a preliminary recorded volume hologram. The hologram is disposed throughout a support medium which is analyte sensitive. The process of detection consists of variation of one or more optical characteristics of the hologram due to variation (s) in the hologram support medium caused by the reaction of the analyte in liquid form with a substance disposed throughout the sensor. One of the problems associated with such a hologram is that it is necessary to immerse the sensor in liquid to detect a colour change.

The present invention is aimed at addressing the above problems.

STATEMENTS OF INVENTION

According to the invention there is provided a sensor device comprising a holographic element comprising a grating or hologram recorded in a holographic recording medium wherein at least one physical and/or chemical and/or optical characteristic of the holographic element or the image produced by it varies as a result of variation in relative humidity or moisture content.

In one aspect the invention provides a sensor device comprising a holographic element comprising a grating or hologram recorded in a holographic recording medium wherein at least one physical and/or chemical and/or optical characteristic of the holographic element or the image produced by it varies as a result of variation in moisture content of the environment exposed to the element.

The moisture content may vary as a result of a change in relative humidity.

Alternatively or additionally, the moisture content varies as a result of breathing.

The invention also provides a sensor device comprising a holographic element comprising a grating recorded in a holographic recording medium, wherein at least one physical and/or chemical and/or optical characteristic of the holographic element varies as a result of variation in an environmental property.

The device may be configured to sense variation in environmental temperature.

The device may be configured to sense variation in environmental pressure.

In one embodiment the grating comprises a constant or spatially varying fringe spacing.

The thickness of the holographic element may vary in response to variation of relative or moisture content.

The spacing between the fringes of the grating may vary in response to variation in relative humidity or moisture content.

In one embodiment the reconstruction wavelength of the holographic element varies in response to variation in relative humidity or moisture content.

In one case the holographic element comprises a reflection grating.

The holographic element may comprise a transmission grating.

In one embodiment the device is passive.

In one case the device is configured to provide an output visible to the naked eye. The device may provide an output visible under ambient light.

In one embodiment the device may comprise a holographic element configured to provide an indication of changes in relative humidity or moisture content. The holographic element may be configured to provide an indication of the maximum or minimum relative humidity to which it has been exposed.

In one embodiment the device further comprises a reference element.

The holographic recording medium may not degrade in humid conditions and/or may not comprise a memory.

In one case the device comprises a holographic recording configured to respond irreversibly to humidity.

In one embodiment the device comprises a holographic recording configured to respond to a particular level or range of relative humidity.

In one case the holographic recording medium comprises a layered structure.

The holographic recording medium may comprise a photopolymer.

In one embodiment the holographic recording medium comprises a hygroscopic material.

In one case the holographic recording medium comprises an acrylamide or polyacrylamide material.

In one embodiment the holographic recording medium comprises an acrylamide monomer. In one case the acrylamide is present at a concentration range of from 12% to 19% wt.

In one embodiment the holographic recording medium comprises a binder. The binder may comprise polyvinyl alcohol (PVA). The PVA is preferably partially hydrolysed. The PVA may have a percentage hydrolysis of about 80%. The PVA may have a molecular weight of less than about 30,000. The PVA preferably has a molecular weight in the range of from about 8,000 to about 9,000.

In one embodiment the holographic recording medium comprises an electron donor. In one case the electron donor comprises Triethanolamine. The triethanolamine may be present at a concentration in the range of about 26.7% to about 51.9% wt.

In one embodiment the holographic recording medium comprises a sensitizer. The sensitizer may comprises a photosensitive dye. The photosensitive dye may comprises Erythrosin B, or any other Xanthene dye, or any dye that produces a significant number of triplet states with long enough lifetime upon photoexcitation.

In one embodiment the holographic recording medium comprises a cross-linking monomer. The cross-linking monomer may comprise NN'methylenebisacrylamide.

The bisacrylamide is preferably present at a concentration in the range of from about 3.9% to about 6.6% wt.

In one embodiment the holographic recording medium comprises a film

The holographic recording medium may be non-toxic and/or chemically inert.

The invention also provides packaging incorporating a sensor device of the invention.

The invention also provides a security hologram that changes its appearance when breathed on.

In another aspect the invention provides a sensor device comprising a holographic element comprising a grating recorded in a holographic recording medium, wherein at least one physical and/or chemical and/or optical characteristic of the holographic element varies as a result of variation in an environmental property, especially relative humidity or moisture content, or possibly environmental temperature, or possibly environmental pressure.

In another aspect the invention provides a device wherein the hologram is a reflection hologram recorded in a dry, acrylamide based photopolymer material, the hologram having a diffraction efficiency greater than 25% at spatial frequencies greater than 4500 lines mm$^{-1}$. In one embodiment the hologram has a diffraction efficiency of greater than 30% as spatial frequencies greater than 4500 lines mm$^{-1}$.

In the device a holographic image or text may disappear by shifting its colour from the visible wavelengths into the infrared or UV wavelengths, or appear by shifting from the infrared or UV wavelengths into the visible wavelengths.

The invention further provides a packaging incorporating a sensor device of the invention.

The invention also provides a security hologram incorporating a sensor device of the invention.

The invention also provides an acrylamide based photopolymer material incorporating a monomer, a cross-linking monomer, a photosensitive dye, an initiator, and a polymeric binder, capable of forming, without treatment, development or processing following recording, a reflection hologram having a diffraction efficiency of greater than 25 per cent at spatial frequencies greater than 4500 lines per mm. In one embodiment the reflection hologram has a diffraction efficiency of greater than 30% at spatial frequencies greater than 4500 lines mm$^{-1}$.

In one embodiment the holographic recording medium comprises an acrylamide monomer. In one case the acrylamide is present at a concentration range of from 12% to 19% wt.

In one embodiment the holographic recording medium comprises a binder. The binder may comprise polyvinyl alcohol (PVA). The PVA is preferably partially hydrolysed. The PVA may have a percentage hydrolysis of about 80%. The PVA may have a molecular weight of less than about 30,000. The PVA preferably has a molecular weight in the range of from about 8,000 to about 9,000.

In one embodiment the holographic recording medium comprises an electron donor. In one case the electron donor comprises Triethanolamine. The triethanolamine may be present at a concentration in the range of about 26.7% to about 51.9% wt.

In one embodiment the holographic recording medium comprises a sensitizer. The sensitizer may comprises a photosensitive dye. The photosensitive dye may comprises Erythrosin B, or any other Xanthene dye, or any dye that produces a significant number of triplet states with long enough lifetime upon photoexcitation.

In one embodiment the holographic recording medium comprises a cross-linking monomer. The cross-linking monomer may comprise NN'methylenebisacrylamide. The bisacrylamide is preferably present at a concentration in the range of from about 3.9% to about 6.6% wt.

The invention further provides a reflection hologram recorded in a dry, acrylamide based photopolymer material, the hologram having a diffraction efficiency greater than 25% at spatial frequencies greater than 4500 lines mm$^{-1}$. In one embodiment the reflection hologram has a diffraction efficiency of greater than 30% at spatial frequencies greater than 4500 lines mm$^{-1}$.

In one embodiment the holographic recording medium comprises an acrylamide monomer. In one case the acrylamide is present at a concentration range of from 12% to 19% wt.

In one embodiment the holographic recording medium comprises a binder. The binder may comprise polyvinyl alcohol (PVA). The PVA is preferably partially hydrolysed. The PVA may have a percentage hydrolysis of about 80%. The PVA may have a molecular weight of less than about 30,000. The PVA preferably has a molecular weight in the range of from about 8,000 to about 9,000.

In one embodiment the holographic recording medium comprises an electron donor. In one case the electron donor comprises Triethanolamine. The triethanolamine may be present at a concentration in the range of about 26.7% to about 51.9% wt.

In one embodiment the holographic recording medium comprises a sensitizer. The sensitizer may comprises a photosensitive dye. The photosensitive dye may comprises Erythrosin B, or any other Xanthene dye, or any dye that produces a significant number of triplet states with long enough lifetime upon photoexcitation.

In one embodiment the holographic recording medium comprises a cross-linking monomer. The cross-linking monomer may comprise NN'methylenebisacrylamide. The bisacrylamide is preferably present at a concentration in the range of from about 3.9% to about 6.6% wt.

The hologram may be prepared using the material of the invention which is irradiated with ultraviolet light after recording for the purpose of polymerising any remaining acrylamide to ensure non-toxicity.

The hologram may be prepared using the material of the invention, which is heated after recording with the purpose of controlling the colour response to change in humidity.

The hologram may be prepared using the material of the invention, which is heated after recording for the purpose of changing the hologram's spectral response, response to moisture, or altering the diffraction efficiency, wavelength or angular selectivity or temporal stability characteristics.

BRIEF DESCRIPTION OF THE DRAWINGS

The invention will be more clearly understood from the following description of some embodiments thereof given by way of example only with reference to the accompanying drawings, in which:

FIGS. 2(a) and 2(b) are illustrations of a sensor device according to the invention in use to provide a reading of relative humidity at high and low humidity respectively;

FIG. 12 is a graph which shows the dynamics of the position of the maximum intensity in the spectral response of a reflection grating after exposure to 60% RH. The thickness of the grating is 30 μm. This rapid response is particularly suitable for security applications as the hologram changes colour quickly when breathed on.

DETAILED DESCRIPTION

Figure 1:
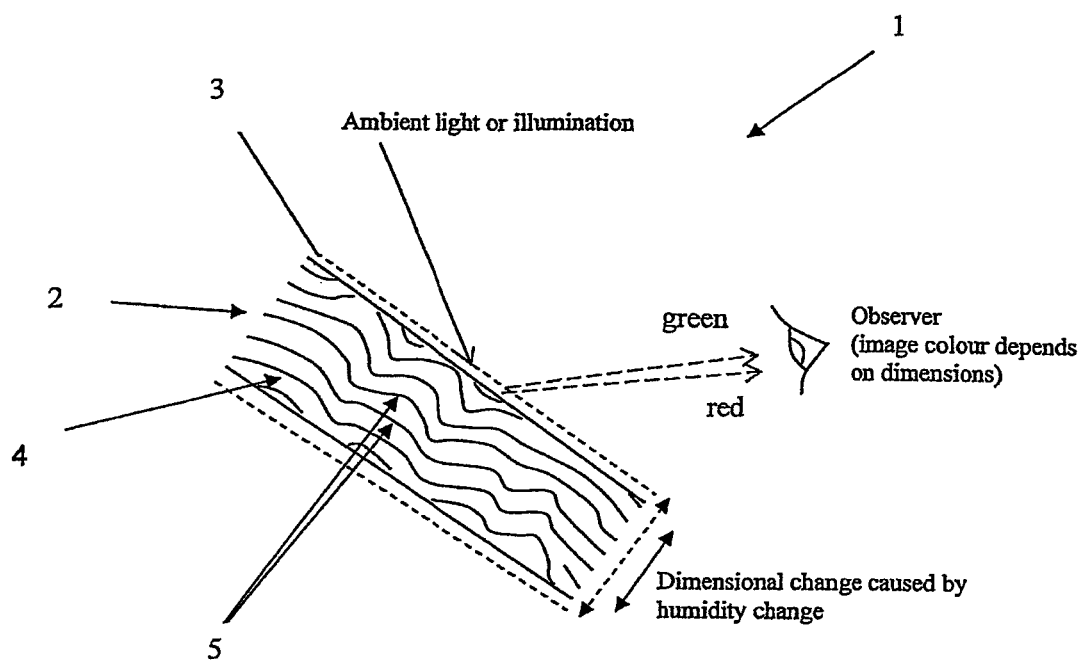
FIG. 1 is a diagram of a sensor device according to the invention.

Referring to the drawings and initially FIG. 1 a sensor device 1 comprises a holographic element 2. The holographic element 2 comprises a holographic grating 4 recorded in a holographic recording medium 3. The grating 4 comprises a fixed or spatially varying spacing produced by recording an interference pattern in the holographic recording medium 3. The holographic recording medium 3 comprises a photosensitive medium. In the above and throughout the specification the term grating has been used to refer to an interference pattern recorded in a holographic recording medium. However, it will be appreciated that the device of the invention may comprise either a grating or a hologram recorded in a holographic recording medium.

In this case the holographic element 2 is configured such that a variation in the physical and/or chemical and/or optical characteristics of the element is produced as a result of variation in relative humidity. The sensor device 1 thus provides an indication of variation in relative humidity.

In this case, the holographic grating 4 recorded in the holographic recording medium 3 comprises a reflection grating and the holographic recording medium includes a hygroscopic material or materials such as an acrylamide, or polyacrylamide, or polyvinylalcohol, as will be described in more detail below.

Figures 2, 2B:
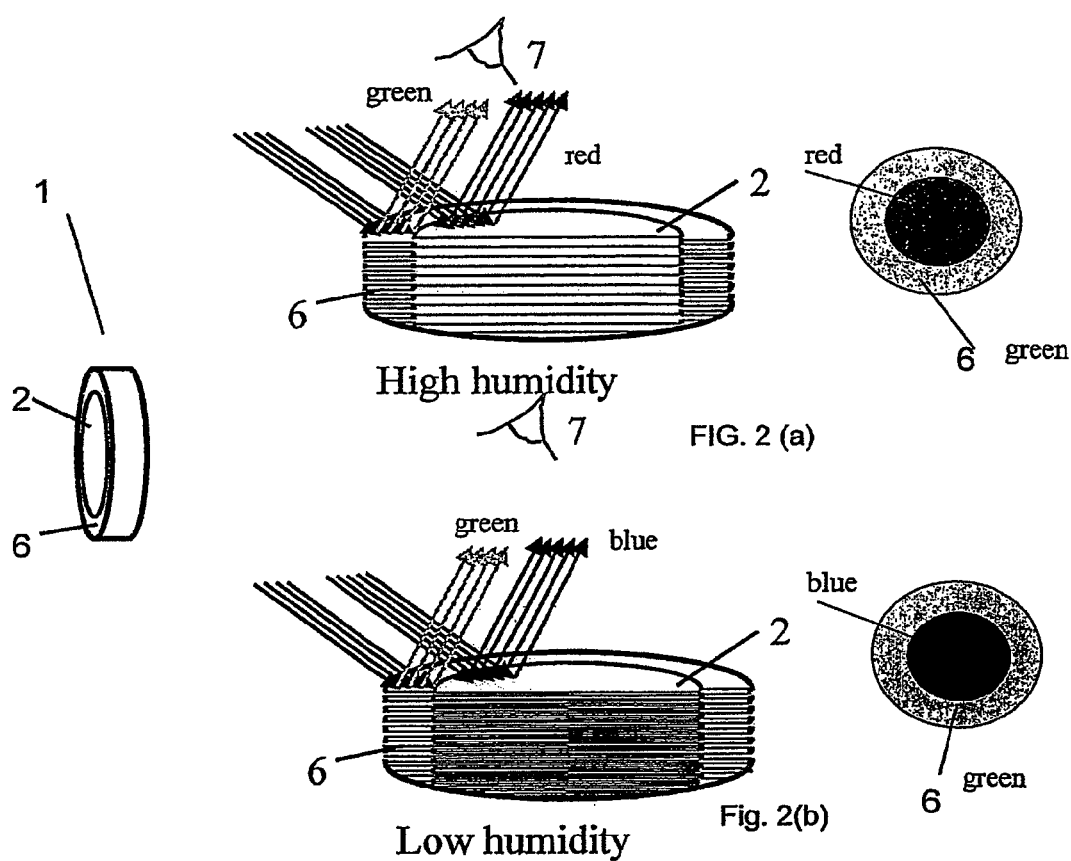

Referring to FIG. 2, in an alternative embodiment the sensor device 1 comprises a first holographic element 2 and a second reference element 6 arranged side by side. The reference element 6 is configured for example by sealing or by material design and/or formulation so that it will not respond to humidity/moisture and will act as a reference. Heating at high temperature can also change the sensitivity of the device to humidity change. The provision of a reference element facilitates ease of reading of the sensor device 1 by an observer 7 and provides a contrasting element. There may be more than one reference element.

The wavelength of light reconstructed by a reflection grating or hologram depends on the spacing of the fringes or planes 5 of the grating or hologram 4. In this case, the reflection grating 4 recorded in the holographic recording medium 3 changes thickness in proportion to the relative humidity of the environment. As the relative humidity changes the grating 4 swells (FIG. 2(*a*)) or shrinks (FIG. 2(*b*)) and the apparent colour observed or detected changes correspondingly.

The sensor device 1 is a passive device operable without a power source, electronics, or detector system. Changes in relative humidity are indicated by a simple colour change and require only ambient light. The increase in local humidity can be caused by breathing on the device.

Figure 3:
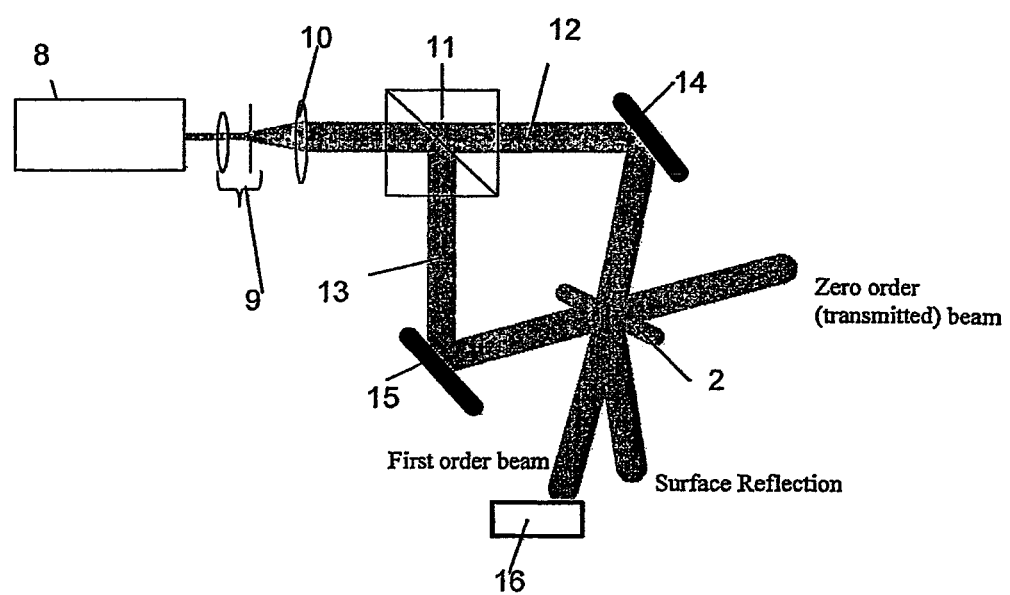
FIG. 3 is a diagram of an experimental set-up for preparing a sensor device according to the invention.
Figure 4:
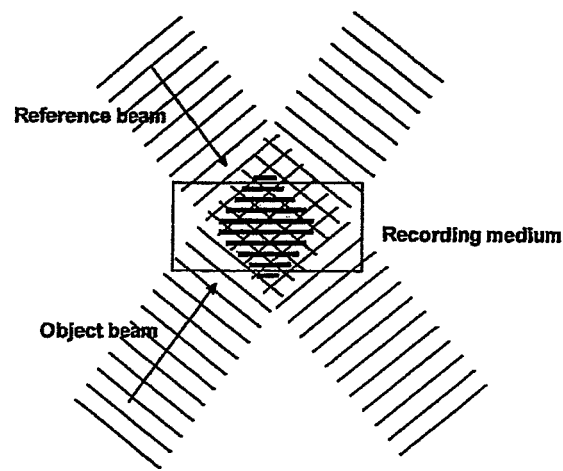
FIG. 4 is a diagram of a reflection grating recorded by the method of FIG. 3.
Figure 5:
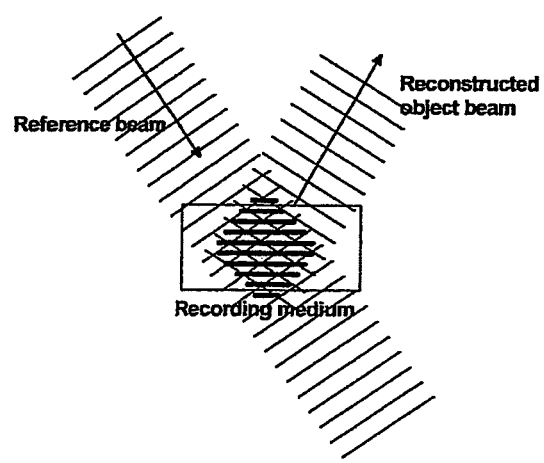
FIG. 5 is a diagram showing the reconstruction of a light beam from the reflection grating of FIG. 4.

Referring to FIGS. 3 to 5, a method for recording and reconstructing a reflection hologram grating 4 is described. Light from a laser 8 is spatially filtered and collimated at a spatial filter 9 and collimator 10. This collimated light is split into two beams 12 and 13 after passing through a beam splitter 11. The two beams 12, 13 are diverted onto the holographic recording medium 2 using two adjustable mirrors 14 and 15 and a reflection holographic grating 4 is recorded. The angle between the recording beams together with the chosen recording wavelength determine the initial spatial frequency of the grating 4 according to equation 1.

$$2n\Lambda \sin(\theta) = \lambda \qquad \text{Equation 1}$$

where '$\lambda$' is the recording wavelength (here 0.532 μm) '$\Lambda$' is the fringe spacing of the recorded hologram, '$n$' is the refractive index of photopolymer composition (here ~1.50) and '$\theta$' is the half the interbeam recording angle in the photopolymer layer. The fringes are, in effect, layers in the medium, whose refractive index is changed from the surrounding regions by the reaction of the material to the interference pattern produced by the two light beams. In order to separate the first order and specularly reflected beams on reconstruction, gratings 4 were recorded with a very small slant angle, that is that the bisector of the angle between the beams was not the normal. The normal is a straight line perpendicular to the plane of the surface to the surface of the photosensitive medium.

The diffraction efficiency of the recorded reflection grating is measured using a photodetector 16.

In an alternative arrangement, one of the recording beams 12 or 13 may have its wavefront spatially modulated by passage through an optical device such as a lens or ground glass, spatial light modulator or by reflection from an object. In such cases the spacing $\Lambda$ in the hologram varies according to location in the holographic recording medium. A hologram may be produced which shows an image of the object.

Referring to FIG. 5 reconstruction of a recorded reflection grating or hologram, is described. During reconstruction, the object beam is blocked and the grating/hologram is illuminated with the reference beam. A reconstruction of the object beam is observed.

In the case of the grating, on reconstruction with a white light source, or observation in ambient light, light of substantially the same colour as the light of the recording laser is observed. In the case of the hologram, an image of the original object is reconstructed in light substantially the same colour of the recording laser light. In each case, colour may differ slightly due to initial shrinkage.

In the reflection grating 4, because the fringes are parallel rather than perpendicular to the plane of the substrate, a change in physical dimensions of the grating such as in the thickness thereof due to swelling or shrinking is represented by a shift in the reconstruction wavelength. In this case, a 3.3% thickness change in a reflection grating spacing corresponded to a colour shift from blue (493 nm) to green (510 nm).

The holographic recording medium 3 can comprise a photopolymer layer composition including the following: a binder, which acts as a support medium or host matrix for monomers acrylamide and bisacrylamide an electron donor and a sensitizer.

In more detail, the structure of a holographic recording medium 3 according to the invention, which has been found to provide particularly good results, includes the following
Monomer:

The primary monomer used in the photopolymer composition of the invention is Acrylamide. The structure of the acrylamide molecule is shown below. The molecules contain a carbon-carbon double bond (C=C). This double bond is broken on polymerization resulting in two single bonds. Electrophoresis grade acrylamide powder (for example, from Sigma Aldrich) was used. We have found that the acrylamide concentration in a dry photopolymer layer for recording both high efficiency transmission and reflection holograms ranges from about 12 to about 19% wt. we have found that an acrylamide concentration of about 12.6% produces excellent transmission holograms. An acrylaimide concentration of about 18% produces excellent reflection holograms.

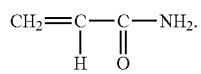

Binder:

The binder used in the photopolymer layer may be polyvinyl alcohol (PVA) (for example from Sigma Aldrich or Riedel De Haen). The chemical formula of pure polyvinyl alcohol (100% hydrolyzed) binder is shown below.

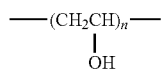

We have found that a binder with a low percentage hydrolysis is particularly useful for recording efficient reflection holograms as such binders have lower permeability and thus inhibit diffusion of polymer away from the regions where it has been formed. A low molecular weight is also generally preferred as this will dissolve more readily in water. The binder may have a hydrolysis percentage of less than 85%, (most preferably about 80%) and a molecular weight of less than 30,000 (most preferably in the range of about 8000 to about 9000). The chemical formula of an alternative lower percentage hydrolyzed polyvinyl alcohol in which a second polymer (generally polyvinyl acetate, from which the polyvinyl alcohol is synthesized) is as follows

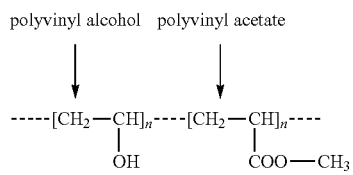

Crosslinking Monomer:

The second monomer used in the photopolymer layer composition which acts as a crosslinking monomer was NN'methylenebisacrylamide (from Sigma Aldrich). The structure of the molecule is shown below. It is a symmetric molecule of two acrylamide molecules attached with a methyl group in the middle.

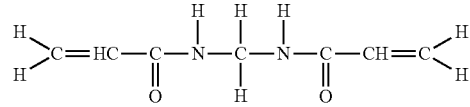 [SMILES: C=CC(=O)NCNC(=O)C=C]

We have found that the bisacrylamide concentration in a dry photopolymer layer for recording both high efficiency transmission and reflection holograms preferably ranges from 3.9% to 6.6% wt. A bisacrylamide concentration of about 4.2% produces excellent transmission holograms. A bisacrylamide concentration of about 5.6% produces excellent reflection holograms.
Electron Donor:

The electron donor may comprise Triethanolamine (TEA) (from Sigma Aldrich chemicals), which plays a significant role in the generation of free radicals to initiate a polymerization reaction and also stabilizes the recording layer, preventing the precipitation of acrylamide onto the layer surface. The chemical formula of TEA is shown below.

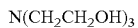

We have found that the triethanolamine concentration in a dry photopolymer layer for recording both high efficiency transmission and reflection holograms preferably ranges from 26.7% to 51.9% wt. A triethanolamine concentration of about 46.3% produces excellent transmission holograms. A triethanolamine concentration of about 37.1% produces excellent reflection holograms. Triethanolamine also acts as a plasticizer and facilitates diffusion. Its concentration is reduced for reflection holography so that polymer diffusion is inhibited.
Sensitizer The sensitizer may comprise a photosensitive dye, for example Erythrosin B (from Sigma Aldrich chemicals). Erythrosin B is green light sensitive dye having a complex structure with four benzene rings. The structure of the molecule is shown below.

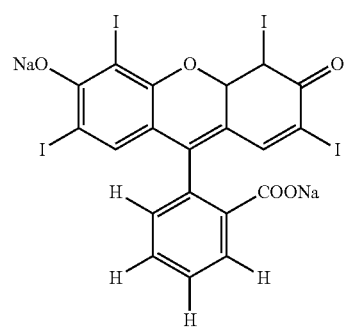

Mechanism of Recording:

The basic composition is two polymerizable monomers (acrylamide and NN'methylenebisacrylamide), a photosensitizer 14 (Erythrosin B), an electron donor (Triethanolamine) and a binder (Polyvinyl alcohol). In this photopolymer, NN'methylenebisacrylamide acts as a crosslinking monomer and polyvinyl alcohol acts as a binder (matrix) within which all other components are suspended.

The refractive index modulation produced when a hologram or grating 4 is recorded in a photopolymerizable material is a result of several reaction steps (processes).

The photosensitive dye (Erythrosin B) is exposed to a light of appropriate wavelength and a primary photoprocess ensues. The dye (XD) absorbs a photon of the light and enters into an excited singlet state ($^1XD^*$)

$$XD+h\nu \rightarrow {}^1XD^*$$

This may either revert to the ground state by emission of a photon (fluorescence) or by radiationless transfer to another molecule e.g. the electron donor (ED), (fluorescence quenching)

$$^1XD^* \rightarrow XD+h\nu_{(fluorescence)}$$

$$^1XD^*+ED \rightarrow XD+ED^* \text{(fluorescence quenching)}$$

or it may cross over to the more stable long lived lower excited triplet state ($^3XD^*$) (intersystem crossing).

$$^1XD^* \rightarrow {}^3XD^* \text{(intersystem crossing)}$$

Triethanolamine donates an electron to the excited triplet state of the dye molecule leaving the latter with one unpaired electron and an overall negative charge.

$$^3XD^*+(HOCH_2CH_2)_3N: \rightarrow XD.^- +(HOCH_2CH_2)_3N.^+$$

The triethanolamine radical cation then loses a proton and becomes an uncharged free radical.

$$(HOCH_2CH_2)_3N.^+ \rightarrow (HOCH_2CH_2)_2NCH.CH_2OH+H^+$$

The triethanolamine radical produced in the above reaction is the initiating species for the polymerization process.

This free radical in the presence of monomer molecule (acrylamide) can react in two ways. The first way is that it can react with dye radical to form a leuco (colourless) form of the dye (thereby using up the dye radicals) or it can react with a monomer to initiate free radical polymerization.

The free radical attacks the double bond on the monomer and links itself to the monomer molecule, which thereby becomes a free radical and repeats the process. The chain reaction results in the growing of the polymer chain, which will continue until all the monomer is consumed or termination occurs. Polymerisation is accompanied by diffusion of monomer from unilluminated regions of destructive light interference into the illuminated regions of constructive light interference driven by concentration gradients created by non-uniform polymerization thus increasing the density in illuminated regions. Counter diffusion of short polymer chains could also occur and this would cause a fall in diffraction efficiency especially at higher spatial frequencies. For this reason, special attention must be given to control of the permeability of the material as indicated above, by proper choice of binder and initiator concentrations. It is the change in local refractive index, through the density and polarizability changes brought about by polymerization which records the hologram. The final hologram comprises a spatial modulation of the refractive index which relates to the spatial variation of intensity in the original interference pattern.

The recording conditions of light intensity and exposure time also play an important role as the intensity is believed to determine the size of polymer chains, lower intensities producing longer chains and higher intensities producing shorter ones which can more readily diffuse away from where they were formed. We have found that the preferable range of intensity is from 1.5 to 10 mW cm$^{-2}$ and exposure times from 20 to 60 seconds for both transmission and reflection holographic recording. The maximum diffraction efficiency obtained in transmission mode of recording is 100%. The maximum diffraction efficiency obtained in reflection mode of recording is currently 30%. We know of no higher value for diffraction efficiency in reflection holograms in acrylamide based photopolymers.

While the above described holographic recording medium has been found to provide particularly good results, it will be appreciated that a suitable alternative medium according to the invention may also be used.

Suitable holographic recording media may be comprised of alternative monomers, binders, sensitizers, and electron donors.

Any suitable monomers may be used such as acrylamides, for example:
N,N-Diethyl acrylamide, Tradename: DEAA;
N,N Dimethyl acrylamide, Tradename: NNDMA;
N-Isopropyl acrylamide, Tradename: NIPAM;
N-(2-Hydroxyethyl acrylamide), Tradename: HEAA; or
2-Hydroxyethyl methacrylate, Tradename-HEMA
Alternatively the monomer may be an acrylate such as:
N,N Dimethylaminoethyl Acrylate; or
N,N Dimethylaminoethyl Methacrylate
Any suitable binders may be used such as:
Polyvinylpirrolidone;
A sol-gel;
A hydrogel;
An acrylate;
Polyethyleneoxide;
Polyethyleneglycol; or
Polyethyloxazaline.
Any suitable electron donors may be used such as N-phenylglycine (NPG), which may be used in combination with diphenyliodonium Hexafluorophosphate (DPI).
Any suitable sensitisers may be used such as:
Erythrosin B;
Methylene blue;
Eosin yellowish;
Ethyl Eosine;
Eosine Scarlet;
Phloxine B;
Fluorescein;
An xanthene dye;
A quinine-imine dye, for example Safranin O, or
A thionine dye
The media may comprise any suitable additives such as:
Nanosize organic and/or inorganic additives having a tendency to retain/release water that is different to that of host photopolymer;
Nanosize organic and inorganic additives having optical or physical characteristics that alter the diffraction efficiency, diffusion properties or spatial frequency response of the photopolymer recording material;
Liquid crystals; or
Chemically inert substances intended to alter the refractive index profile in the recorded grating or hologram.

Example 1

A holographic element 2 according to the invention may comprise a slanted transmission grating recorded in a holographic recording medium. This provides a sensor device 1 having Bragg angle dependence on relative humidity. The dimensional change due to change in environmental relative humidity is detected from the shift in the Bragg angle for reconstruction. In such a case the angular shift in the output beam is detected using a laser light source and a detector. This detector could be position or intensity sensitive to provide a precise measurement of relative humidity.

A method of preparation of a holographic recording medium 3 and a holographic element 2 which in this specific case is a slanted transmission holographic grating, according to the invention includes some or all or the following steps:
Stock Solution of Polyvinyl Alcohol (PVA):

10 grams of PVA of specified molecular weight and hydrolysis is dissolved in 100 ml of water to prepare a 9.1% by weight or 10% w/v PVA solution.
Stock Solution of Dye:

0.1100 grams of Erythrosin B dye are dissolved in 100 ml of water to prepare 0.11% w/v of dye solution, and stored in darkness.
Composition of Photosensitive Medium:

A composition of the photosensitive medium is prepared by adding 2 ml of triethanolamine to 0.2 grams of NN'methylenebisacrylamide (crosslinking monomer) and 0.6 grams of acrylamide (monomer). To this mixture, 17.5 ml of stock solution of 9.1% polyvinyl alcohol is then added and the total solution is stirred thoroughly, to ensure the monomer and crosslinking monomer are completely dissolved to obtain a homogenous solution. Finally 4 ml of the 0.11% w/v stock solution of dye is added to the above solution in darkness and mixed thoroughly to get a fine, low scattering, liquid photopolymer solution.
Layer Preparation:

1.5 ml of photopolymer solution is spread uniformly on a 50×50 mm$^2$ glass plate placed on a levelled surface and allowed to dry forming a film. The drying time is usually 36-48 hours. The thicknesses of the photopolymer film layers thus formed are approximately 120 μm to 140 μm.

Figure 6:
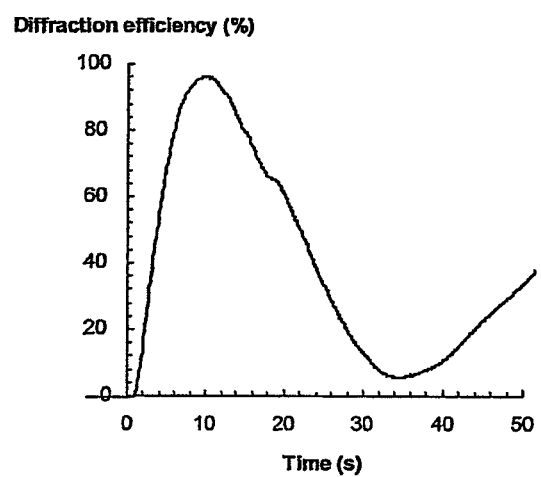
FIG. 6 is a graph showing the diffraction efficiency as a function of exposure time for a 300 lines/mm grating according to the invention, recorded with a total intensity of 4 mW/cm$^2$.

Referring to FIG. 6, a typical growth curve for the diffraction efficiency of a transmission grating of example 1 monitored in real time during recording is shown. As shown, the diffraction efficiency approaches 100% and then decreases, due to overmodulation (i.e. further increase in the refractive index modulation), as the diffracted light is coupled back into the zero order.

Figure 7:
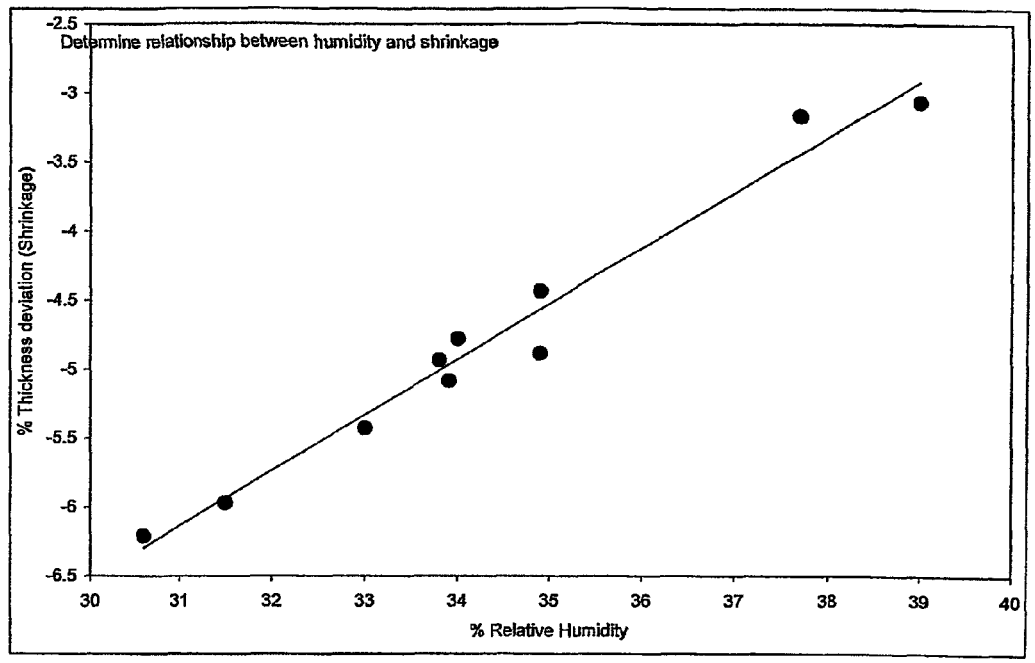
FIG. 7 is a graph showing the relationship between the environmental relative humidity and the shrinkage of a slanted transmission holographic element according to the invention.

Referring to FIG. 7 the relationship is shown between the environmental relative humidity and the shrinkage of a holographic element according to the invention.

In an alternative embodiment, the hologram may be recorded with the fringes slanted at an angle to the surface of the photosensitive medium and the hologram may be subsequently illuminated by light entering at the edge of the glass plate. Such light will then be reflected or diffracted by the recorded fringes to emerge parallel to or nearly parallel to the normal to the surface. The angle or colour or phase of the emerging light will change with fringe spacing. Thus a change in the angle or colour may be used to detect and measure changes in an environmental quantity such as relative humidity.

In an alternative embodiment, two or more holograms may be recorded in the same layer such that at a specific range of humidity only one reconstruction is detected.

Example 2

Highly efficient reflection holograms can be recorded for bright reconstruction in applications such as security and humidity/moisture sensing, but also in display holography, memory applications and any application where high efficiency of the hologram is important.

In order to prepare photopolymer solution for recording reflection holograms 0.8 grams of acrylamide, 0.25 grams of NN'methylenebisacrylamide and 1.5 ml TEA were added to 17.5 ml of 10% w/v PVA stock solution. The PVA stock solution was prepared by dissolving 10 grams of PVA of molecular weight 8000-9000 and 80% hydrolysis in 100 ml of deionised water. The solution was mixed for 30 min at room temperature until it turns into colourless transparent liquid. Then 3 ml of Erythrosine B dye sensitizer 0.11% w/v stock solution were added to the solution and mixed for another 5 min at room temperature. The dye stock solution was previously prepared by dissolving 0.11 grams of Erythrosine B dye in 100 ml of deionised, and stored in darkness until required.

The photosensitive layers were prepared by coating the photopolymer solution on 5×5 cm$^2$ glass plates. In order to obtain approximately 30 μm, 60 μm or 90 μm thick layers respectively 0.5 ml, 1 ml and 1.5 ml of photopolymer solution must be deposited on the glass plate.

The layers were dried in dark for 24 hours after coating at room temperature and relative humidity between 30 and 50%.

A 30% diffraction efficiency reflection grating of spatial frequency of 4600 lines/mm was recorded in 60 μm thick layers by using 532 nm laser beam with intensity of 10 mW/cm$^2$ and exposure time 40 s.

Figure 8:
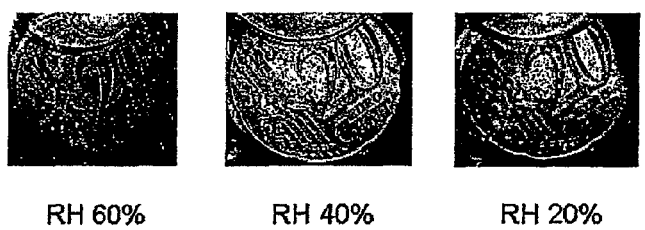
FIG. 8 shows digital photographs of a hologram of a coin changing colour in changing humidity conditions. At RH 60%—red colour, RH 40%—green colour and at RH 20%—blue colour.

Bright Denisyuk holograms were recorded in layers of thickness 30 μm. The intensity of recording was 3 mW/cm$^2$ and the exposure time was 40 s. FIG. 8 shows how a typical such hologram changes colour with change in humidity.

Figure 9:
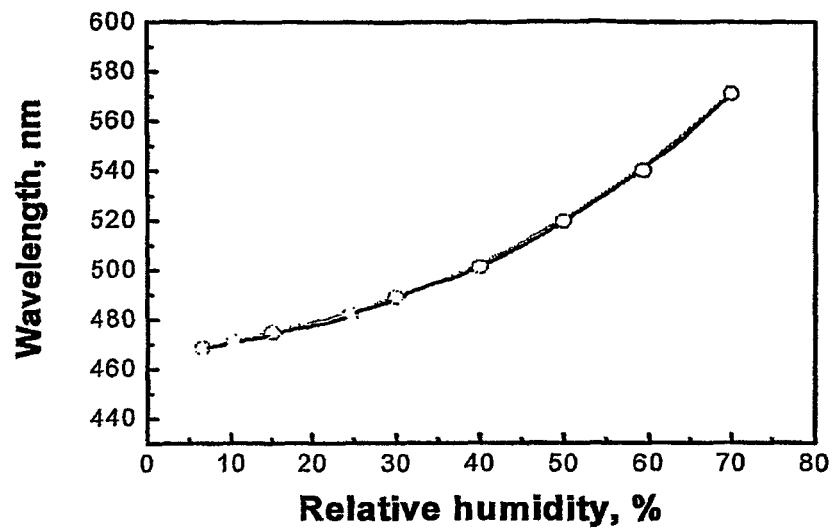
FIG. 9 is a graph showing the relationship between the environmental relative humidity and the wavelength of the light reconstructed by a reflection holographic grating according to the invention.
Figure 10:
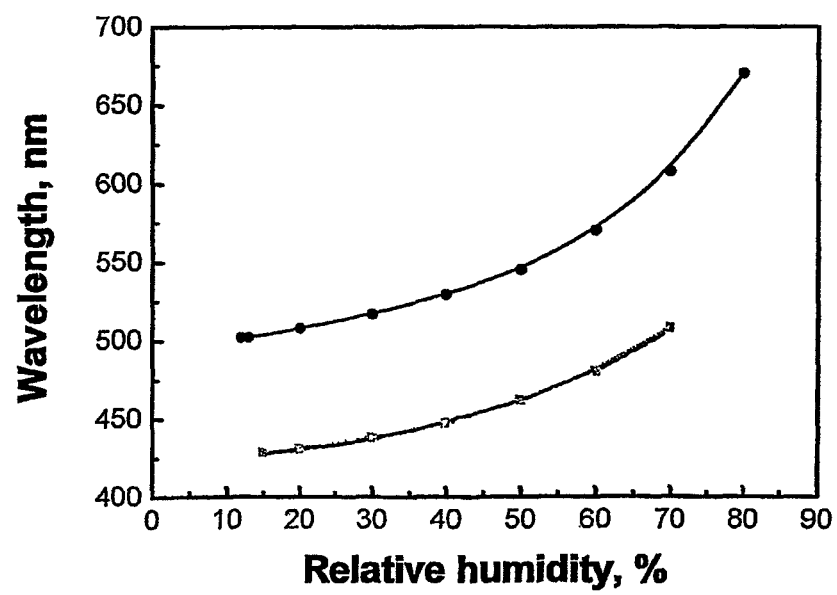
FIG. 10 shows the effect of heating the holographic grating to 125° C.

A typical graph showing the change in the wavelength of the light diffracted by a reflection grating as the humidity changes is given in FIG. 9. The grating was recorded at a relative humidity of 38%, Following the procedure for sample preparation described in this example a reflection hologram of a mirror was recorded by using 532 nm laser beam, intensity of recording 3 mW/cm$^2$ and recording time of 40 s. The relative humidity at the time of recording was 29%. The response of the hologram when exposed to a range of humidity was measured before and after heating the hologram to different temperatures in the range of 100-145° C. It was observed that the heating of the hologram to high temperature leads to a shift in the calibration curve (FIG. 10). In FIG. 10 the upper curve was obtained before the grating was heated. The lower curve was obtained following heating of the grating for 30 minutes at 145° C. The shift is most probably due to irreversible shrinkage of the hologram. The shift in the calibration curve can be used to adjust the exact colour of the hologram at a specific humidity. It can also be used to make hologram invisible at a specific humidity, as it will reconstruct the image in the UV spectral range, and appear only when exposed to humidity higher than this specific humidity. This can also be achieved by recording at short wavelengths and/or high humidity so that in normal humidity the reconstruction is shifted towards the blue end of the spectrum. A similar effect can be achieved when recording occurs at low humidity and long wavelengths in which case at normal humidity the reconstruction wavelength will be shifted into the IR region and will not be visible until the humidity drops sufficiently for the red image to appear.

The holographic recording medium 3 is designed so that it will not degrade in humid conditions and does not comprise a memory. In other words the invention provides a device which gives a changing and potentially real-time indication of the relative humidity. The device is installed as required and may be used over a period of time to indicate changing relative humidity.

The sensor of the invention is designed to take account of conditions of the environment in which it is to be used. For example, a holographic recording medium which is non-toxic and thus suitable for use in proximity to food is selected if the sensor is to be used in proximity to food.

The sensor is also configurable for use in an environment having a particular range of levels of humidity, in which case, the sensor is designed for operation in that range.

While in the embodiment described, the holographic recording medium does not degrade in humid conditions and does not comprise a memory, it will be appreciated that in an alternative embodiment, a holographic recording medium according to the invention may be provided which responds irreversibly to humidity, or is designed to degrade on exposure to a certain level of humidity, depending on the requirements and applications.

A sensor device according to the invention comprising a holographic element recorded in such a recording medium would respond irreversibly to relative humidity so that the device acts as an indicator of the highest or lowest relative humidity experienced when exposed. This may be achieved by including a reference hologram fabricated in a photopolymer layer together with a hologram fabricated in a photopolymer layer doped with zeolite nanoparticles. If the zeolite doped hologram behaves differently after exposure to a humid environment for some time, there will be a mismatch in the colours of the two holograms. It may also be possible to drive off the water from the zeolites before exposure by dessication, or after exposure by heating so as to improve the response.

As described above, the sensor device may comprise a first holographic element 2 and a second reference element 6 as shown in FIG. 2.

It will be appreciated that in a further embodiment, two or more different holograms may be recorded in the same layer such that at a specific range of relative humidity, reconstruction from only one is visible. This has the advantage of providing a more distinctive display for the user. More than one image can be made visible to the user to indicate, for example, different levels of relative humidity, or to display a security message such as 'valid' or 'original copy'.

In further alternative embodiments, the sensor device according to the invention may comprise any combination of holographic elements configured for a changing or real-time indication of humidity, and/or indication of the highest or lowest relative humidity experienced, and/or a reference element.

Also while in the embodiment described the detected physical property is relative humidity, it will be appreciated that the holographic element may also be configured to detect other physical properties for example, temperature or pressure.

The sensor device in this example of the invention has the advantage that it is a passive device. There is no need to use a power source, electronics, or detector system. The device has the advantage that it is a stand alone device. Changes in relative humidity are indicated by a simple colour change using only ambient light.

The device of the invention has the further advantage that it is lightweight. For example the holographic element typically comprises a film having a thickness of between 30 and 200 microns. However, it will be appreciated that the thickness of the film may vary depending on material used and requirements. The device is also very robust and flexible. The material in which it is made has the advantage that it is self developing and requires no chemical or physical processing. This is a significant advantage in mass production.

The device of the invention has the advantage that a single element may be used to indicate a whole range of relative humidity levels, the relative humidity being indicated by the colour of the light diffracted by the element.

Other possible uses or applications of the sensor device of the invention include the following: mounting in domestic environments, building materials, greenhouses, storage areas, refrigerators, industrial environments, archiving areas or museums. The device may also be incorporated into packaging for electronics and integrated circuits, foodstuffs (such as fruit and vegetables, flour and other dry goods), clothing, pharmaceuticals, vitamins and food supplements. Another important application may include using the device as a security label to protect against counterfeiting. Another important application may include the sensing of a break in the integrity of a package.

The holographic recording medium of the invention has advantages as an optical recording material for reflection holography including the following: high sensitivity, capability of achieving 30% diffraction efficiency, self processing, low cost, high signal to noise ratio, and capability of being prepared in thicker layers with ease.

Example 3

In this case the moisture sensitive hologram is used as an authentication device or security hologram.

Figure 11:
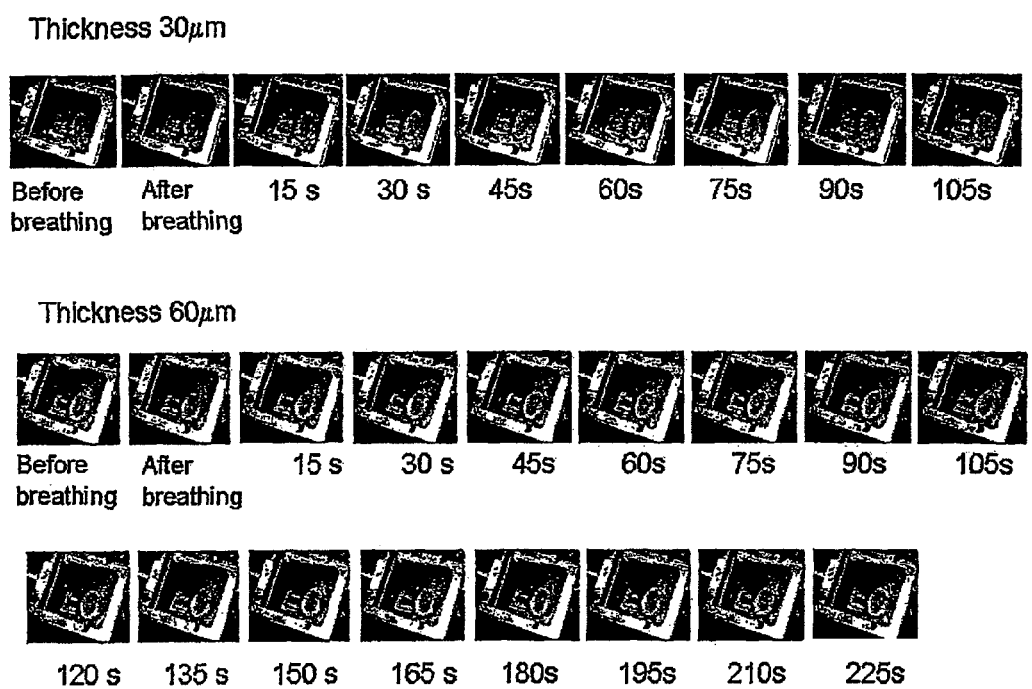
FIG. 11 illustrates the time response of the reversible change in the colour after the sensor/hologram has been breathed on. The hologram changes colour from green to red initially when breathed on. A sensor/hologram prepared in a 30 μm thick layer returns to the green colour in 75 seconds after which there is no further change and a 60 μm thick layer returns in 165 second after which there is no further change. The thicker hologram responds more slowly.

Following the procedure for sample preparation and image holograms recording described in Example 2 a hologram comprising the logo of the Centre for Industrial and Engineering Optics at the Dublin Institute of Technology was recorded in a 30 µm thick photopolymer layer. The hologram changes colour from green to red in less than 10 s when breathed on. The original colour is completely restored in 1-2 min (FIG. 11).

The hologram which changes colour or appearance on breathing can be used for the purpose of proving the authenticity of an item (product) or identification of a stolen item (product). It can be part of official document, ballot, diploma certificate, identification card, driving license, passport, business card, cheque book, cheque, share certificate, credit or debit card, banknote, tax banderol, postage stamp, bus, rail or air ticket, event ticket, product label. Being a thin polymer layer it lends itself readily to application onto a document or card, by any of the methods described below for packaging.

The hologram can also be made to appear or disappear on being breathed on or made to display text or messages.

Example 4

The sensor device according to the invention comprises a lightweight film which has the further advantage that it may be incorporated directly into packaging to give a visual indication of environmental relative humidity. A sensor device comprising a non-toxic or chemically inert material may be provided for use with foodstuffs or other sensitive materials as required. In order to ensure non-toxicity all acrylamide remaining after recording the grating or hologram, is converted to polymer by exposure to UV light of spatially uniform intensity.

The sensor device is portable and flexible and may also be incorporated into packaging for other items sensitive to humidity for example, electronic components or building materials. The film may alternatively be incorporated into a sticker for adhesion to packaging or for hanging up in a particular location.

The device of the invention is easy to use and reliable. It furthermore provides information on relative humidity at a glance, increasing consumer confidence. The provision of a reference holographic element in addition to the sensing holographic element further increases the ease of use of the sensor device.

The device of the invention has the further advantage that it may also be used to reconstruct an easily recognizable image, for example that of a company logo, which changes colour with change in environmental conditions. The image itself may change with the environmental conditions.

The device is thus very cost effective from a production and handling point of view. Furthermore the device of the invention is reusable.

The humidity sensitive hologram of the invention may be incorporated in packaging in order to provide an indicator of moisture content or relative humidity and/or serve as a security hologram or authentication device. The hologram is a thin transparent polymer layer which may be readily adhered to flexible plastic packaging such as used in food wrapping or for the protection of electronics or consumer goods, or more rigid polycarbonate used in CD and DVD covers, as well as many other substrates.

The hologram can be recorded using glass as a support for the recording material and then the hologram can be transferred to packaging by self adhesion or using a suitable adhesive, or alternatively the hologram can be recorded on a thin acetate layer which is then glued to the packaging.

Figure 12:
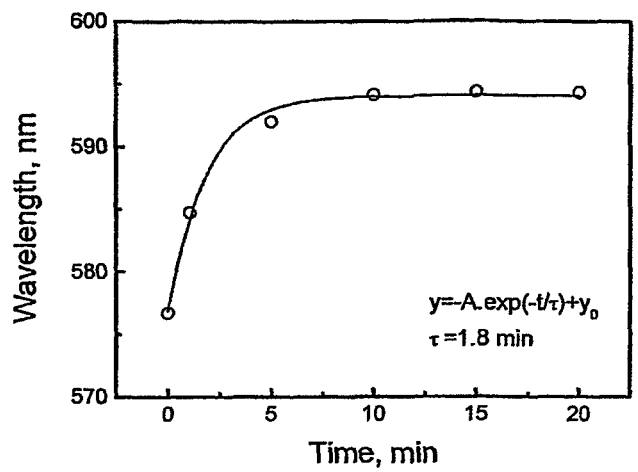

The packaging can be transparent, such as a plastic bottle or container or a flexible plastic membrane, so that the colour of the holographic image can be viewed without exposing the contents of the package. In this case the hologram colour will indicate the moisture content of the internal environment of the package and may have a humidity insensitive holographic element incorporated in which does not change colour or which changes colour within a desirable range. It may be desirable to have a hologram that has a fast response to changes in the internal environment (see FIG. 12).

Figure 13:
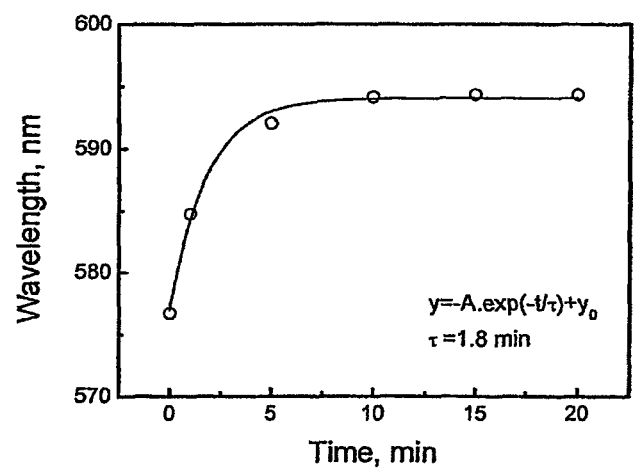
FIG. 13 is a graph which shows the dynamics of the position of the maximum intensity in the spectral response of a reflection grating after exposure to 60% RH. The thickness of the grating is 90 μm. This shows the slower dynamic response of a grating which has a thickness of 90 μm.

In another embodiment the hologram would be placed on an internal surface (e.g. inside the lid of a pharmaceutical container) for viewing after the package has been opened in order to determine the current humidity/moisture content within the package. In this case a slow response may be desirable (see FIG. 13), so that the hologram can be viewed for a few minutes after the package has been opened without changing in response to the external environment. In yet another embodiment the hologram is designed to show or the highest and for lowest humidity to which it has been exposed.

In another embodiment the hologram is used to show that a package has not been tampered with. The package would be sealed at a humidity significantly higher or lower than the normal range (depending on the contents) so that the opening of the package is the cause of a colour change. The hologram colour could be changed further by breathing on it, providing authentication/security function in parallel with the anti-tamper function.

The invention is not limited to the embodiments hereinbefore described which may be varied in detail.

The invention claimed is:

1. An acrylamide based photopolymer material incorporating a monomer, a cross-linking monomer, a photosensitive dye, an initiator, and a polymeric binder, wherein the polymeric binder is polyvinyl alcohol (PVA) with a percentage hydrolysis of about 80% and wherein photopolymer material is capable of forming, without treatment, development or processing following recording, a reflection hologram having a diffraction efficiency of up to 30% at a spatial frequency of 4600 lines per mm.

2. The photopolymer material as claimed in claim 1 comprising an acrylamide monomer.

3. The photopolymer material as claimed in claim 2 wherein the acrylamide is present at a concentration range of from 12% to 19% wt.

4. The photopolymer material as claimed in claim 1 wherein the cross-linking monomer is NN'methylenebisacrylamide.

5. The photopolymer material as claimed in claim 4 wherein the NN'methylenebisacrylamide is present at a concentration in the range of from about 3.9% to about 6.6% wt.

6. The photopolymer material as claimed in claim 1 wherein the initiator is triethanolamine, the triethanolamine may be present at a concentration in the range of about 26.7% to about 51.9% wt.

7. The photopolymer material as claimed in claim 6 wherein the triethanolamine is present at a concentration of about 37.1% wt.

8. The photopolymer material as claimed in claim 1 wherein the dye is a xanthene dye.

9. The photopolymer material as claimed in claim 1 wherein the PVA has a molecular weight of less than about 30,000.

10. The photopolymer material as claimed in claim 9 wherein the PVA has a molecular weight in the range of from about 8,000 to about 9,000.

11. An acrylamide based photopolymer material incorporating a PVA binder having a percentage hydrolysis of about 80% and a molecular weight of less than about 30,000, a monomer, a cross-linking monomer, a photosensitive dye, and an initiator, wherein the photopolymer material is capable of forming, without treatment, development or processing following recording, a reflection hologram having a diffraction efficiency of up to 30% at a spatial frequency of 4600 lines per mm.

12. The photopolymer material as claimed in claim 11 wherein the PVA has a molecular weight in the range of from about 8,000 to about 9,000.

13. The photopolymer material as claimed in claim 11 comprising an acrylamide monomer, the acrylamide may be present at a concentration range of from 12% to 19% wt.

14. The photopolymer material as claimed in claim 11 wherein the cross-linking monomer is NN'methylenebisacrylamide, the NN'methylenebisacrylamide may be present at a concentration in the range of from about 3.9% to about 6.6% wt.

15. The photopolymer material as claimed in claim 11 wherein the initiator is triethanolamine, the triethanolamine may be present at a concentration in the range of about 26.7% to about 51.9% wt.

16. The photopolymer material as claimed in claim 11 wherein the dye is a xanthene dye.

17. The photopolymer material as claimed in claim 15 wherein the triethanolamine is present at a concentration of about 37.1% wt.

* * * * *